United States Patent [19]

Byrum

[11] Plant 4,016

[45] Feb. 8, 1977

[54] ROSE PLANT

[75] Inventor: Roy L. Byrum, Richmond, Ind.

[73] Assignee: Joseph H. Hill Company, Richmond, Ind.

[21] Appl. No.: 662,887

[22] Filed: Mar. 1, 1976

[51] Int. Cl.[2] ..... A01H 5/00

[52] U.S. Cl. ..... Plt./25

[58] Field of Search ..... Plt./22, 25

*Primary Examiner*—Robert E. Bagwill

*Attorney, Agent, or Firm*—Chas. W. Rummler

CLAIM

A new variety of rose plant, suitable for greenhouse culture for the commercial production of cut flowers, particularly distinguished by the warm nasturtium red general color effect of its very double, medium small blossoms. This plant is also characterized by its abundant and continuous production of flowers, which have a slight spicy fragrance and an excellent vase-life as cut flowers, and by its vigorous, upright and much branched growth.

1 Drawing Figure

BACKGROUND OF THE NEW PLANT

My new variety of rose plant was discovered by me at Richmond, Ind., in December 1971 as a sport of the rose plant Gemini (U.S. Plant Pat. No. 2,728). Because of the distinctive and attractive color of this flower, it was promptly taken by me for propagation and successive generations of the resulting plant propagated by budding and grown in greenhouse at Richmond, Ind., have demonstrated that its novel color characteristics are firmly fixed and hold true. Propagation of this new rose plant by budding at Hamilton City, Calif., has also shown that its distinctive characteristics hold true and are firmly fixed.

DESCRIPTION OF THE DRAWING

My new variety of rose plant is illustrated by the accompanying photographic drawing which shows, in full color, the form of the fully opened flower and two stages of its buds, typical leaves, a specimen of old wood, and a specimen of young wood with foliage, the colors being shown as nearly true as it has been possible to obtain by conventional photographic procedures.

DESCRIPTION OF THE NEW PLANT

The following description of my new rose plant sets out its characteristics in detail and comprises data resulting from observations of greenhouse plants grown at Richmond, Ind., in 1975, the color designations being according to Koster's Color Guide (K) and the Horticultural Color Chart (HCC) produced by Robert F. Wilson and published by The Royal Horticultural Society at London, England.

THE PLANT

Origin: Sport.

Parentage: Rose Plant Gemini (U.S. Plant Pat. No. 2,728).

Classification: Floribunda.

Form: Bush.

Habit: Upright and much branched.

Growth: Vigorous.

Canes: Of medium diameter.

Main Stems: Color—Spinach Green 0960/2 (HCC).

*Thorns.*—Several, straight, of medium length and with a short base. Color—Tobacco Brown, Plate 88 (K).

*Prickles.*—Few. Color: Tobacco Brown, Plate 88 (K).

*Hairs.*—None.

Branches: Color—Spinach Green 0960/1 (HCC).

*Thorns.*—Several, of medium length, downwardly hooked and with a narrow base. Color—Chrysanthemum Crimson 824/3 (HCC) tinted at the tip of Pod Green 061/1 (HCC).

*Prickles.*—Few. Color—Chrysanthemum Crimson 824/3 (HCC).

*Hairs.*—None.

New Shoots: Color—Oxblood Red 00823 (HCC).

*Thorns.*—Several, straight, of medium length and with a long, narrow base. Color—Chrysanthemum Crimson 824/3 (HCC) tinted at the tip with Pod Green 061/1 (HCC).

*Prickles.*—Several. Color—Chrysanthemum Crimson 824/3 (HCC).

*Hairs.*—None.

Foliage: Quantity—Abundant.

*Leaves.*—Size—Medium. Shape—Odd pinnate.

*Leaflets.*—3 or 5 in number. Shape—Ovoid, with round base, acuminate apex and simply serrate margin. Color of Leaflets—Mature Leaf: Upper surface: Nearest, Spinach Green 0960 (HCC). Under surface: Spinach Green 0960/3 (HCC). Young Leaf: Upper surface: Fern Green 0862/1 overlaid with Oxblood Red 00823/3 (HCC). Under surface: Fern Green 0862/1 overlaid with Oxblood Red 00823/1 (HCC). Texture—Moderately heavy. Aspect—Glossy.

*Rachis.*—Medium heavy, with grooved and hairy upper side and moderately prickly under side.

*Stipules.*—Of medium length and width, with short points turning out at an angle of less than 45° and recurved toward the stem.

THE BUD

Before Calyx Breaks:

*Size.*—Small.

*Form.*—Short pointed, with a conspicuous neck and with foliaceous appendages on the bud surface which have slender parts extending beyond the bud tip for a distance of one-quarter or more of the bud length.

*Color of Calyx.*—Scheeles Green 860 (HCC).

As Calyx Breaks:

*Color.*—Outside of petals: Mimosa Yellow 602/1 with upper portion Blood Red 820 (HCC).

As First Petal Opens:

*Bud Size.*—Medium small.

*Bud Form.*—Short pointed.

*Color of Petals.*—Outside: Mimosa Yellow 602/1 at the base with the upper portion Fire Red 15/1 (HCC). Inside: Mimosa Yellow 602 at the base with the upper portion of Nasturtium Red 14/1 (HCC) and a white vein extending from the base about two-thirds or more of the petal length.

*Bud Opening.*—Bud opens up very well.

Sepals: Permanent, shear shaped and of medium length.

*Color.*—Inside: Scheeles Green 860/2 (HCC) overlaid with white fuzz. Outside: Scheeles Green 860/1.

Peduncle: Of Medium length and diameter, medium strong and erect.

*Bark.*—Slightly rough. Color—Reseda Red Plate 85 (K).

*Thorns.*—None.

*Prickles.*—None.

*Hairs.*—Few. Color—Nearest—Fuchsine Pink 627/2 (HCC).

THE FLOWER

Blooming Habit: Abundant and continuous.

Size, when fully open: Medium small, 2 to 2¼ inches in diameter.

Borne: One to three to a stem on medium strong stems of medium length.

Shape: Full and high centered at first with the petals rolled outward, becoming flat at maturity with petals loosely rolled outward.

Petalage: Very double with 45 to 50 petals arranged regularly.

*Shape of Petals.*—Outside—Obovate with retuse apex. Intermediate and Inside—Obovate with mucronate apex.

*Texture.*—Moderately thick.

*Aspect.*—Satiny, inside and outside.

Color: A. The following observations were made in October 1975 of a newly opened flower of a greenhouse grown plant.

Outside petals

*Outside Surface.*—Mimosa Yellow 602/1 at the base with Poppy Red 16/1 (HCC) in the upper portion.

*Inside Surface.*—Mimomsa Yellow 602 at the base with Nasturtium Red 14/1 (HCC) in the upper portion.

Intermediate and inner petals

*Outside Surface.*—Mimosa Yellow 602/1 at the base and Poppy Red 16/1 (HCC) in the upper portion.

*Inside Surface.*—Mimosa Yellow 602 at the base and Nasturtium Red 14/1 (HCC) in the upper portion.

Color: B. The following are observations of a flower opened for three days in October 1975.

Outside petals

*Outside Surface.*—Lower portion Mimosa Yellow 602/2 changing to Carmine Rose 621/1 (HCC) at the top.

*Inside Surface.*—Mimosa Yellow 602/1 in lower portion changing to Carmine Rose 621/1 (HCC) at the top.

Intermediate petals

*Outside Surface.*—Mimosa Yellow 602/2 in lower portion changing to Camelia Rose 622/2 (HCC) at the top.

*Inside Surface.*—Mimosa Yellow 602/1 in lower portion changing to Camelia Rose 622/1 (HCC) at the top.

Inner petals

*Outer Surface.*—Mimosa Yellow 602/2 in lower portion changing to Carmine Rose 621/2 (HCC) at the top.

*Inside Surface.*—Mimosa Yellow 602/1 in lower portion changing to Carmine Rose 621 (HCC) at the top.

General Color Effect of Open Bloom:

*Newly Opened Flower.*—Nasturtium Red 14/1 (HCC).

*Three Day Opened Flower.*—Empire Rose 0621 (HCC).

Persistence: Flower petals hang on.

Fragrance: Slight spicy.

Lasting Quality: 5 to 6 days in August at living room temperature.

REPRODUCTIVE ORGANS

Stamens: Of medium number arranged regularly about pistils.

*Filaments.*—Of medium length, most with anthers. Color—Saturn Red 13/1 (HCC).

*Anthers.*—Medium in size—all open at once. Color—Cadmium Orange 8/2 (HCC).

*Pollen.*—Abundant. Color—Orange Buff 507/1 (HCC).

Pistils: Medium in number.

*Styles.*—Even, of medium length, moderately thin and bunched. Color—Solferino Purple 26/1 (HCC).

*Stigma.*—Color—Chinese Yellow 602/2 (HCC).

Ovularies: All encased in calyx.

Hips: None.

Seeds: None.

This new variety of rose plant differs from its parent Gemini mainly by its very distinctive color differential. The new variety is similar to its parent mainly in the shape of the bud and open flower but the flower has more brilliance and luster and the plant has more production than Gemini. The new flower opens well and has excellent vase life as a commercial cut flower and the plant has good growing habits throughout the year.

I claim:

1. A new and distinctive variety of rose plant substantially as herein shown and described, characterized by the distinctive Nasturtium Red to Empire Rose general color effect of the open flowers, by its slightly spicy flower fragrance, its abundant and continuous flower production, and its vigorous year around growth habit.

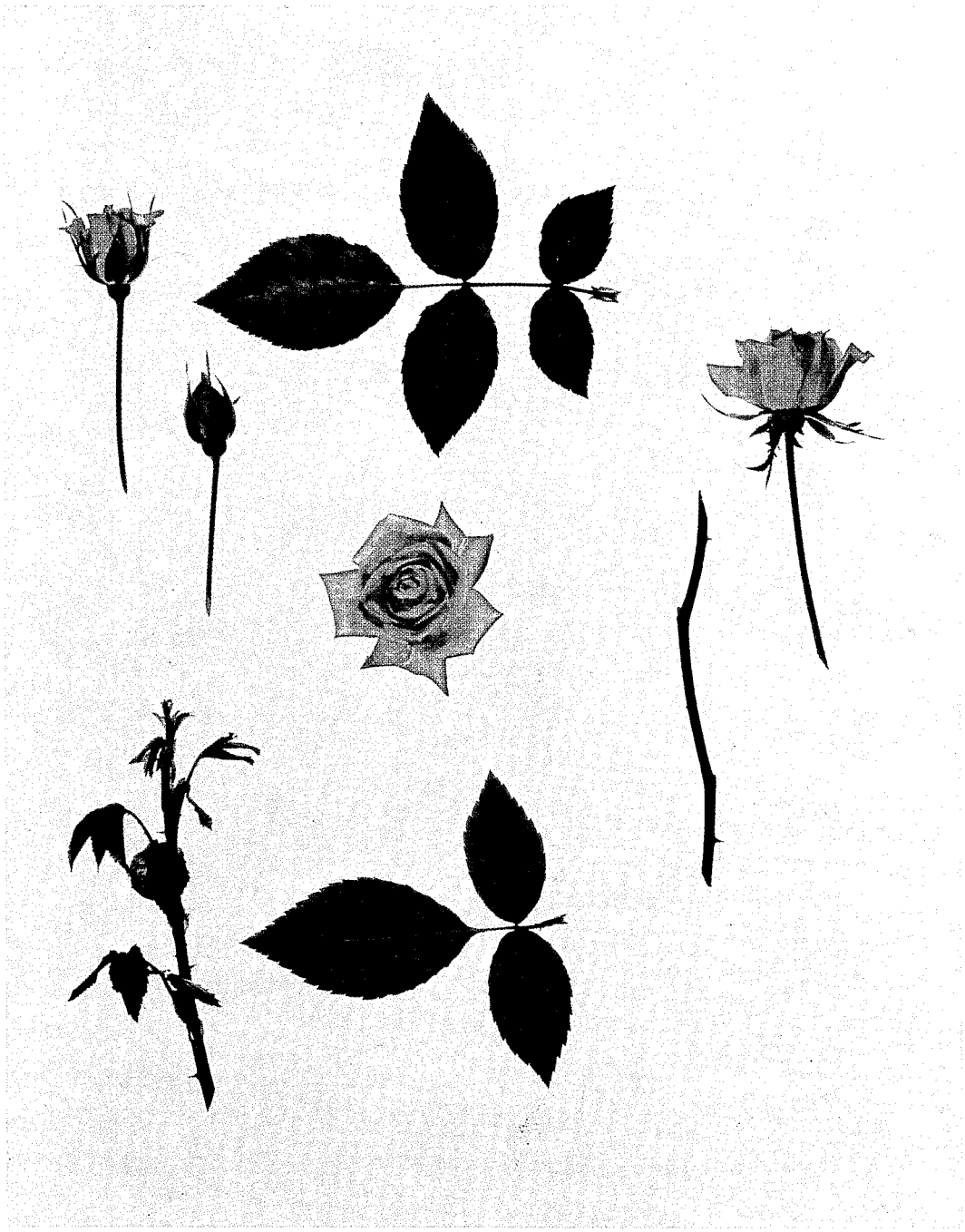

* * * * *